(12) United States Patent
Medoff

(10) Patent No.: US 9,636,157 B2
(45) Date of Patent: May 2, 2017

(54) CONTOURED BONE PLATE FOR FRACTURE FIXATION HAVING HOOK MEMBERS

(75) Inventor: Robert J. Medoff, Kailua, HI (US)

(73) Assignees: Lars G. Tellman, Falsterbo (SE); David Medoff, Valencia, CA (US)

( * ) Notice: Subject to any disclaimer, the term of this patent is extended or adjusted under 35 U.S.C. 154(b) by 956 days.

(21) Appl. No.: 13/103,658

(22) Filed: May 9, 2011

(65) Prior Publication Data
US 2011/0213420 A1    Sep. 1, 2011

Related U.S. Application Data

(62) Division of application No. 12/114,916, filed on May 5, 2008, now Pat. No. 8,177,822.

(51) Int. Cl.
*A61B 17/80* (2006.01)
*A61B 17/17* (2006.01)

(52) U.S. Cl.
CPC ........ *A61B 17/809* (2013.01); *A61B 17/1775* (2016.11); *A61B 17/8061* (2013.01); *A61B 17/1728* (2013.01); *A61B 17/1739* (2013.01)

(58) Field of Classification Search
USPC ..................... 606/74, 75, 280, 297
See application file for complete search history.

(56) References Cited

U.S. PATENT DOCUMENTS

| | | | | |
|---|---|---|---|---|
| 3,554,193 A | * | 1/1971 | Konstantinou et al. | 606/65 |
| 3,824,995 A | * | 7/1974 | Getscher et al. | 606/281 |
| 5,674,222 A | * | 10/1997 | Berger et al. | 606/71 |
| 6,110,190 A | * | 8/2000 | Ginn et al. | 606/190 |
| 6,635,060 B2 | * | 10/2003 | Hanson et al. | 606/79 |
| 7,037,308 B2 | | 5/2006 | Medoff | |
| 2004/0092947 A1 | | 5/2004 | Foley | |

OTHER PUBLICATIONS

Zuelzer, Wilhelm A., Fixation of Small But Important Bone Fragments With a Hook Plate, The Journal of Bone & Joint Surgery, 1951; 33:430-436.
Weseley, M.S., et al., The Use of the Zuelzer Hook Plate in Fixation of Olecranon Fractures, The Journal of Bone & Joint Surgery, 1976; 58:859-863.

* cited by examiner

*Primary Examiner* — Christian Sevilla
(74) *Attorney, Agent, or Firm* — Patzik, Frank & Samotny Ltd.

(57) ABSTRACT

A bone fixation plate for fixation of fractures having a small terminal bone fragment, such as fractures of the lateral malleolus. The bone fixation plate includes an elongated body, and two hook members extending from a first end of the elongated body. Each hook member curves back upon a bottom surface of the elongated body, back towards a second end of the elongated body, and terminating in a pointed prong region. The elongated body includes a first region, a second region, and an angled region disposed between the first and second region. The prong region has a longitudinal axis that is substantially parallel to a longitudinal axis of the angled region of the elongated body of the bone plate.

12 Claims, 12 Drawing Sheets

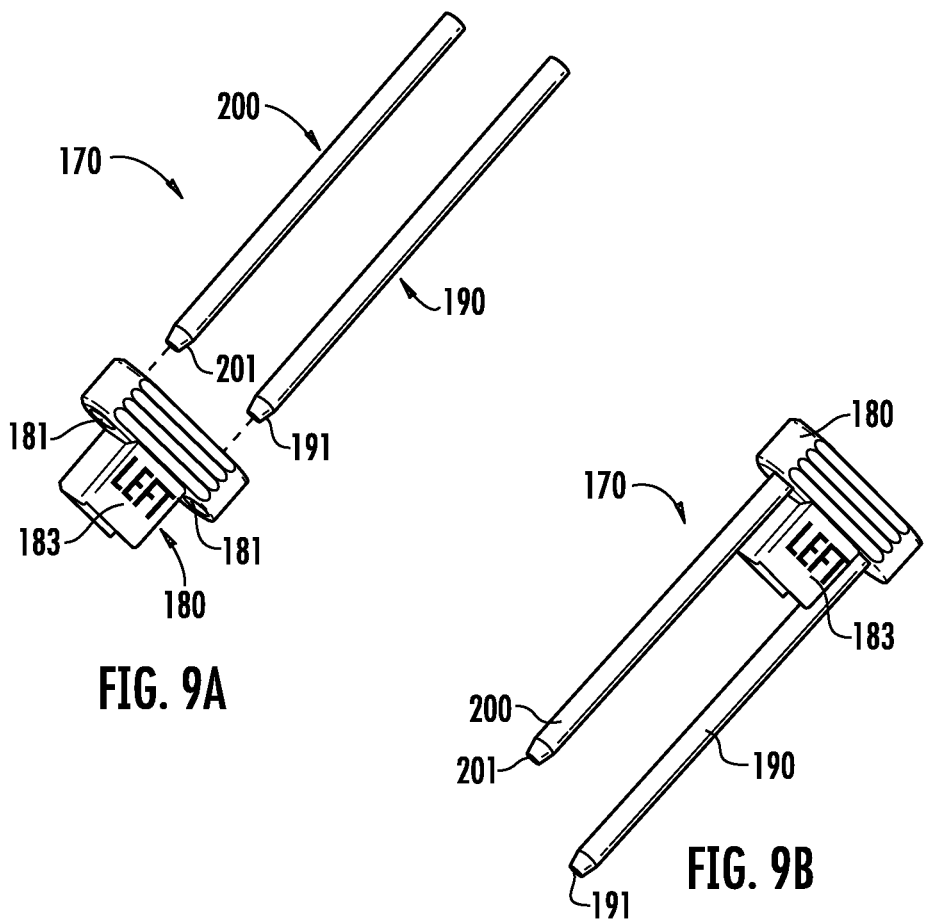
FIG. 9A
FIG. 9B
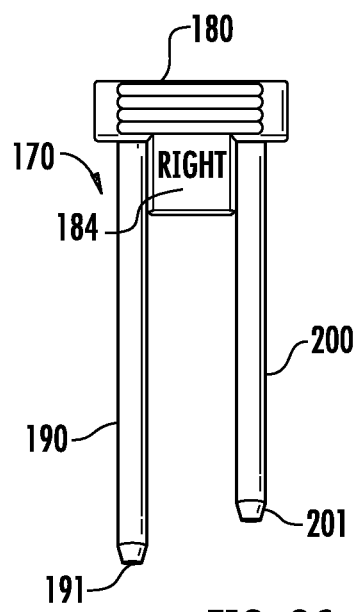
FIG. 9C

CONTOURED BONE PLATE FOR FRACTURE FIXATION HAVING HOOK MEMBERS

CROSS-REFERENCE TO RELATED APPLICATIONS

This application is a division of U.S. application Ser. No. 12/114,916 filed May 5, 2008, the entirety of which is hereby incorporated by reference.

BACKGROUND OF THE INVENTION

1. Field of the Invention

The present invention relates, in general, to the fixation of bone fractures and, more particularly, to the fixation of bone fractures having small fragments proximate a terminal end of a bone.

2. Description of Related Art

Plates and screws are well accepted techniques for fixation of fractures. The standard bone plate is a planar bar of material, usually metal, having circular and/or slotted holes through which bone screws are placed. The bone plate is used to span a fracture and fixation screws are placed through holes in the bone plate positioned on either side of the fracture to secure the bone fragments the plate.

One variation of the standard bone plate is to modify the configuration of the screw holes to help provide compression across the fracture as the screw is placed. Another variation is to include female threads within the perimeter of the bone plate's screw holes, engaging male threads on the head of the screw to lock the screw to the plate.

Difficulties in using bone plates may arise in certain fractures occurring relatively close to the end of a bone, creating a relatively small end fragment. In this situation, there may simply be not enough bone available in the end fragment to accommodate a sufficient number of screws to achieve secure fixation. As a result, a surgeon using a conventional bone plate may use a suboptimal number of screws, which can lead to postoperative failure.

One example of a fracture occurring relatively close to the end of a bone is a fracture of the lateral malleolus, the terminal portion of the fibula that is present on the outside of the ankle, occurring close to its tip. In such situations, only a very small distal fragment may be present, providing inadequate room for more than one or two screws to be placed. Moreover, since the deep portion of this bone is a part of the overall ankle joint, screws cannot be placed through both cortices, as is commonly practice with plate/screw techniques. Accordingly, the surgeon may be faced with the undesirable situation of having the patient leave the operating room with only one or two screws engaging a bone surface directly under a bone plate.

In the past, one technique surgeons have used in an attempt to provide enhanced fixation or grip of a small terminal bone fragment is to begin with a standard plate and cut the plate transversely across at its last screw hole. Using a pair of surgical pliers or other suitable instrument, the remaining bone plate material on opposing sides of the partially remaining hole is bent around the outer surface of the terminal bone fragment. To some degree, this helps supplement the tenuous fixation provided by only one or two screws in the small terminal fragment. However, this terminal bone fragment may still remain far from being well secured.

In another previous technique disclosed in "Use of Zuelzer Hook Plate in the Treatment of Olecranon Fractures" by Wesely, Barenfeld, and Eisenstein, The Journal of Bone & Joint Surgery, Volume 58-A, Issue No 6, September 1976, pages 859-863, a further modification of this technique is described in which a flat plate is pre-contoured with two hooks at one end. The hooks are bent so that they are parallel to the longitudinal axis of the flat plate. The plate is applied to a fractured bone such as the olecranon by manually pressing the hooks into the bone and fixing the plate to the bone surface with screws. Although this technique adds the theoretical advantage of penetration of the terminal fragment with the hooks, if this plate is applied to an anatomic site in which the bone flares out at the terminal end, since the hooks are parallel to the linear axis of the plate, as the hooks are impacted, the plate will not sit flush with the bone surface past the flare at the terminal end but rather come to lie in a position that sits off the bone. In addition, this technique does not address the problem of creating holes in the bone at the correct depth for engagement by the hooks, but rather relies on manual pressure on the plate to attempt penetration of the bone by the hooks at whatever level they happen to contact. As can be noted by the examples in this article, the hooks may fail to penetrate the bone resulting in less than satisfactory engagement and fixation of the terminal fragment by the hooks as well as prominence of the hooks in the soft tissue because of incomplete seating. Finally, since these implants have hooks that extend an equal distance from the end of the plate, this design does not allow completely seating of both hooks in the common situation in which the bone surface at the terminal end is at an angle to the plane that is perpendicular to the long axis of the bone.

Accordingly, it is an object of the present invention to provide a bone plate that adequately secures a small bone fragment at a terminal end of a bone.

It is a further object of the present invention to provide a bone plate that can be seated flush against a bone characterized by a flare at the terminal segment, yet sill providing full engagement of the small terminal fragment by complete seating of one or more hooks into bone. It is a further object of the present invention to provide a means to create pilot holes in the terminal fragment for engagement by the hooks in the plate such that the hook or hooks in the plate engage the bone at the correct depth and trajectory so as to direct the plate to advance both longitudinally as well as drop down against the surface of the bone as it is seated.

It is another object of the present invention to provide a design that has a contour that approximates the flare of the terminal segment of a bone as well as provides one or more hooks that are angled along an axis that approximates the best linear fit approximation of such flare.

It is another object of the present invention to provide a drill guide facilitating accurate placement of a bone plate proximate a terminal end of a bone.

These and other objects and features of the present invention will become apparent in view of the present specification, drawing and claims.

BRIEF SUMMARY OF THE INVENTION

The present invention comprises a bone plate for fixing fractures having a small terminal fragment. The bone plate has an elongated body having a first end, a second end, a top surface, a bottom surface, and an angled or curved flared region disposed between the first end and the second end that can be described by a best fit first longitudinal axis. At least one hook member is provided proximate the first end and has a prong region having a second longitudinal axis. Moreover, the first longitudinal axis and the second longitudinal axis are substantially parallel to each other.

In one preferred embodiment of the present invention, the at least one hook member comprises a first hook member and a second hook member, with each of the first and second hook members having a prong region with a second longitudinal axis substantially parallel to the first longitudinal axis. The first hook member has a first curved region including a first apex, the second curved member has a second curved region including a second apex, and the distance between the second end and the first apex is greater than the distance between the second end and the second apex. In another preferred embodiment, the distance between the second end to the first apex is equal to the distance between the second end to the second apex.

Moreover, in a preferred embodiment, the elongated body includes a first region and a second region on opposing sides of the angled region, with the first region, angled region, and second region collectively form a surface substantially corresponding to the surface contour of the human fibula at the lateral malleolus. Other embodiments contemplated by the present invention may be formed with the angled region designed to conform to the contour of other sites of application in which the bone surface flares superficially at the terminal end, such as the olecranon, proximal ulna, proximal or distal humerus, medial malleolus, or similar bones. The elongated body preferably includes at least one bone screw accepting hole extending therethrough, and at least a portion of the bottom surface of the elongated body has a concave curvature. This concave curvature is dimensioned to substantially correspond to the surface curvature of the human fibula proximate the lateral malleolus. Moreover, the at least one hook member has a curved region curving from the elongated body proximate the first end, back towards the second end of the elongated body and terminating in the prong region.

The present invention also comprises a multiple barreled drill guide facilitating the drilling of at least two parallel holes at the distal end of a bone at the correct depth. The multiple barreled drill guide has a body, at least two sleeves coupled to the body in substantially parallel orientation relative to each other, with each sleeve having a first longitudinal axis, and an elongated positioning member extending from the body and having a second longitudinal axis. The first longitudinal axis may be angled relative to the second longitudinal axis such that, when the drill guide is positioned with the elongated positioning member disposed along a distal end of a human fibula and the sleeves abutting a terminal end of the fibula, the first longitudinal axis of each sleeve extends into the lateral malleolus of the fibula. In a preferred embodiment, this angle between the first longitudinal axis and the second longitudinal axis is approximately three degrees. In another preferred embodiment, the first longitudinal axis and second longitudinal axis are parallel.

The double barreled drill guide further includes a cooperating inner drill guide configured to releasably engage the multiple barreled drill guide. The inner drill guide includes an inner drill guide body, and at least two inner sleeves coupled to the inner drill guide body, with at least a portion of each of the inner sleeves being aligned by the inner drill guide body for axial insertion into at least a portion of a corresponding sleeve of the multiple barreled drill guide. In one variation of the inner drill guide, at least one of the inner sleeves includes an internal channel sized to accommodate a 0.9 mm Kirshner wire, with an other diameter of 2.0 mm to fit in the double barreled guide which can accept a 2.0 mm drill.

The double barreled drill guide further includes a gauge configured to releasably engage the multiple barreled drill guide. The gauge has a gauge body, a first elongated member coupled to the gauge body and having a first end, a second elongated member coupled to the gauge body and having a second end. At least a portion of the first and second elongated members are aligned by the gauge body for axial insertion into at least a portion of a corresponding sleeve of the multiple barreled drill guide. Moreover, the first and second elongated members are of unequal length. The gauge further includes indicia disposed on the gauge body and indicating a current orientation of the gauge.

BRIEF DESCRIPTION OF THE SEVERAL VIEWS OF THE DRAWINGS

FIG. 9A is an exploded left perspective view of the gauge assembly;

FIG. 9B is a left perspective view of the gauge assembly;

FIG. 9C is a top view of the gauge assembly;

DETAILED DESCRIPTION OF THE INVENTION

Figure 1:
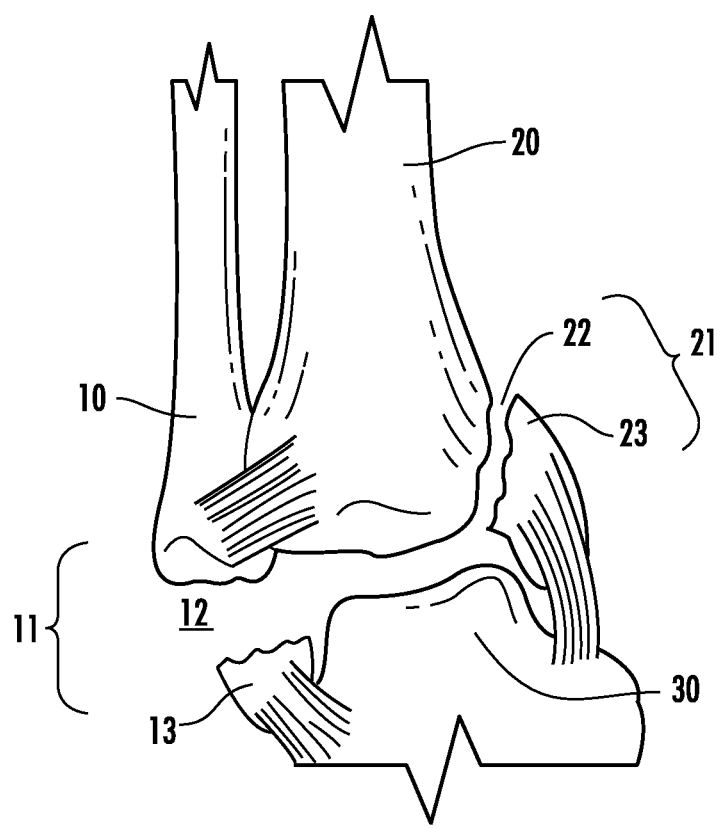
FIG. 1 is a simplified anterior view of a portion of the human right ankle, showing fractures of both the lateral malleolus of the fibula and medial malleolus of the tibia.

While several different embodiments of the present invention are described herein and shown in the various figures, common reference numerals in the figures denote similar or analogous elements or structure amongst the various embodiments.

A simplified anterior view of a portion of the right human ankle is shown in FIG. 1 as comprising fibula 10, tibia 20, and talus 30. Right fibula 10 is shown having a fracture of the lateral malleolus 11 thereof, creating a small terminal fragment 13 proximate fracture site 12. Simultaneously, right tibia 20 is shown having a fracture of the medial malleolus 21 thereof, creating a small terminal fragment 23 proximate fracture site 22.

Figure 2A:
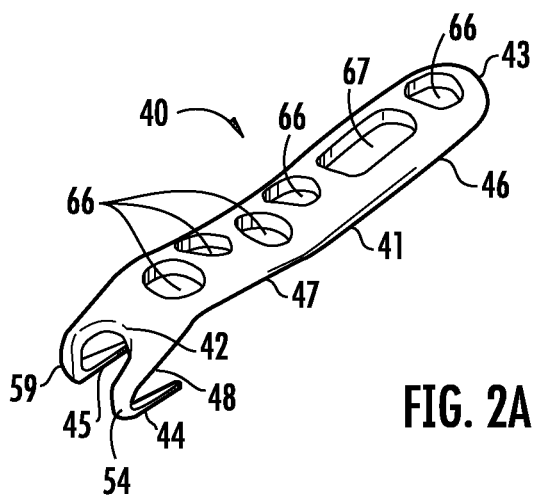
FIG. 2A is a perspective view of a 6-hole left offset fracture fixation plate of the present invention, configured for use in the fixation of certain fractures of the ankle.
Figure 2B:
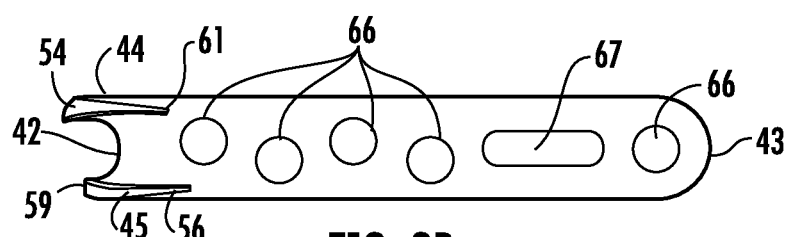
FIG. 2B is a bottom view of the 6-hole left offset fracture fixation plate.
Figure 2C:
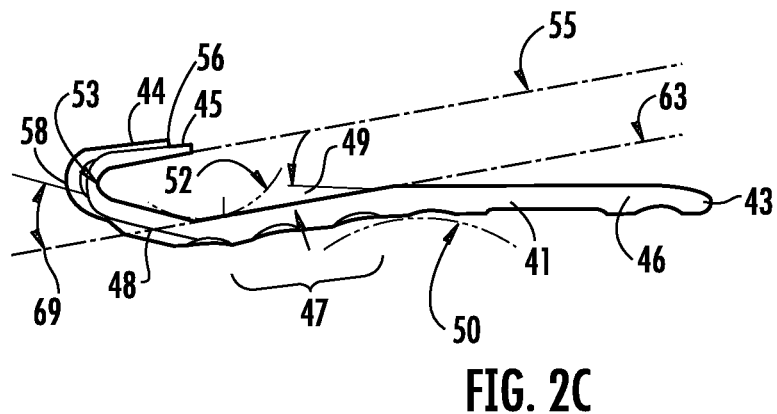
FIG. 2C is a right side view of the 6-hole left offset fracture fixation plate.
Figure 2D:
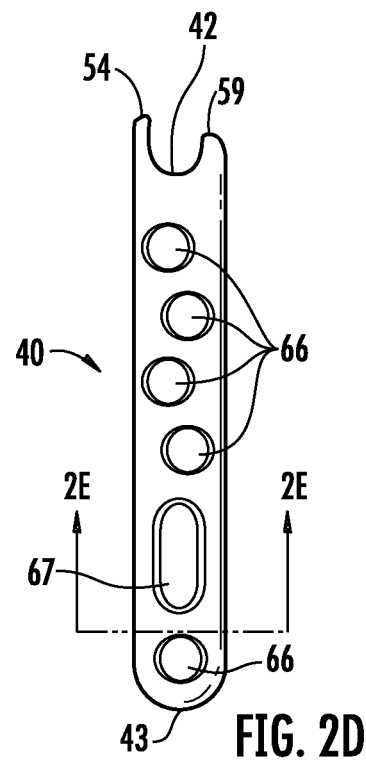
FIG. 2D is a top plan view of the 6-hole left offset fracture fixation plate.

A six-hole left offset bone plate 40 of the present invention, configured for use in conjunction with fractures of the lateral malleolus, is shown in FIGS. 2A through 2F as comprising an elongated body 41, having a first end 42 proximate first hook member, or tooth member 44 and second hook member, or tooth member 45. Elongated body 41 includes a first region 48 proximate first end 42, a second region 46 proximate a second end 43, and an intermediate, angled, or "flared" region 47 disposed between first region 48 and second region 46. Elongated body 41 includes a plurality of apertures extending therethrough for use in conjunction with conventional bone screws, including five circular holes 66, and one slotted hole 67. As best seen in FIGS. 2B and 2D, circular holes 66 are in a collectively staggered off-center orientation, relative to a longitudinal axis of elongated body 41, while slotted hole 67 is centered along this longitudinal axis. Moreover, and as best seen in FIG. 2A, slotted hole 67 and each circular hole 66 includes an associated countersunk, beveled perimeter, relative to the top surface of elongated body 41, facilitating the frusto-conical heads of conventional bone screws to be fully seated against, and hence in securing engagement with, an associated hole upon implantation.

As best seen in FIG. 2C, angled region 47 is generally defined and created by the presence of first radius of curvature 52 relative to the bottom surface of bone plate 40 proximate the juncture of substantially linear first region 48 and substantially linear angled region 47; together with the presence of second radius of curvature 50 relative to the top surface of bone plate 40 proximate the juncture of substantially linear second region 46 and angled region 47. The length of the linear angled region 47 and the inclination defined as the angle 49 between a line 63 parallel to linear angled region 47 with the longitudinal axis of the elongated body 41, substantially match the length and inclination of the flare of the associated bone requiring fracture fixation. It should be noted that substantially linear first region 48 may in fact be a curved surface that may be approximated by a best fit inclination angle 49. As a result, the bottom surface of elongated body 41 bone plate 40 has an overall longitudinal contour which substantially corresponds to the flared profile of the distal end of the human fibula proximate the lateral malleolus. These values, including the lengths of angled region 47, first region 48, and second region 46, radii of curvature 50 and 52, and angles 49 and 69, may be modified during the manufacturing process to create a hooked bone plate specifically tailored for other sites of application having a bone surface flare superficially proximate the terminal end, such as the medial malleolus, olecranon, proximal ulna, proximal femur, proximal fifth metatarsal, proximal or distal humerus, or other such sites of application.

In one preferred embodiment, the length, contour and relative angling of linear angled region 47, relative to first region 48 and second region 46, is designed and to match the flare of the surface contour of the site of application using an electronically scanned or mathematical three-dimensional model of the site of application, such as the lateral malleolus or olecranon as examples. In particular, a three-dimensional mathematical model of a particular bone having a flared surface region proximate its terminal end is created, using a three-dimensional scan of either an actual human bone or an artificial model of a human bone, or a three-dimensional model created entirely by computer. Computer aided drafting software is then used in conjunction with this three-dimensional mathematical model of the bone to create a bone plate of the present invention having a back surface profile of angled region 47, first region 48 and second region 46 such that, when the prong members are impacted proximate the terminal end of the bone, this back surface profile substantially corresponds to the adjacent flared contour of the bone, such that the bone plate rests substantially adjacent the bone.

Referring to FIG. 2C, in a preferred embodiment of a six-hole hook plate of the present invention, wherein the instrument has an overall length of approximately 2.874 inches, and a length of elongated body 41 between first end 42 and second end 43 of approximately 2.278 inches, first angle of curvature 52 has a radius of approximately 0.380 inches, yielding a first curved bend angle 69 of approximately 25° at the junction of the bottom surface of angled region 47 and the bottom surface of first region 48 of elongated body 41. Moreover, for this embodiment of a six-hole hook plate of the present invention, second angle of curvature 50 has a radius of approximately 0.500 inches, yielding a second curved bend angle 49 of approximately 10° at the junction of the bottom surface of angled region 47 and the bottom surface of second region 46 of elongated body 41. Although, in a preferred embodiment, these two bend angles are achieved through curvature of portions elongated body 41, sharper bends, rather than more gentle curves, may alternatively be used.

First hook member 44 includes curved region 58, having an apex 54 and curving from first region 48 of elongated body 41, curving back upon the bottom surface of elongated body 41, back towards second end 43 and terminating in first pointed prong region 61. Similarly, second hook member 45 includes curved region 53, having an apex 59 and curving from first region 48 of elongated body 41, curving back upon the bottom surface of elongated body 41, back towards second end 43 and terminating in second pointed prong region 56. In a preferred embodiment of a six-hole hook plate of the present invention, wherein the instrument has an overall length of approximately 2.874 inches, and a length of elongated body 41 between first end 42 and second end 43 of approximately 2.278 inches, first prong region 61 and second prong region 56 both have a length of approximately 0.390 inches, as measured from apex to tip.

In the left offset plate, and as best seen in FIGS. 2B and 2D, hook plate 40 is not bilaterally symmetrical, relative to the longitudinal axis of elongated body 41. In particular, curved region 58 and its apex 54 of first hook member 44 is more distally spaced than curved region 53 and its apex 59, relative to both first end 42 and second end 43 of elongated body 41. In particular, in a preferred embodiment, apex 54 of first hook member 44 extends approximately 2 millimeters farther than apex 59 of second hook member 45, relative to second end 41 of elongated body 41. This asymmetrical configuration permits hook members 44 and 45, hook plate 40 overall, to more closely approximate the often asymmetric contour of the distal surface of the fibula at the lateral malleolus, upon securement of hook plate 40 across the fracture site. In another embodiment, the surgeon is provided with a selection of plates in which the apex 54 of first hook 44 extends the same distance as the apex of 59 of the second hook member 45 (i.e., a bilaterally symmetrical hook plate); as well as a plate in which the apex 59 of second hook 45 extends 2 mm farther than the apex 54 of first hook 44 (i.e., a right offset plate). It can be seen by those skilled in the art that these variations can be values other than 2 mm and are intended to accommodate variability of the surface anatomy at the site of application.

Figure 2E:
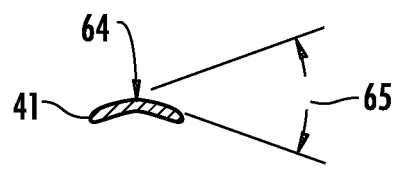
FIG. 2E is a sectional view of the 6-hole left offset fracture fixation plate, taken generally along lines 2E-2E of FIG. 2D.
Figure 2F:
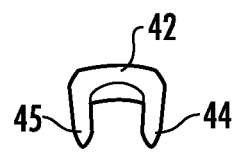
FIG. 2F is a front view of the 6-hole left offset fracture fixation plate.

As best seen in FIG. 2E, hook plate 40 has an arcuate cross section and bottom surface, along substantially all of the length of elongated body 41. This curved bottom surface permits hook plate 40 to more closely approximate the curved longitudinal surface of the fibula, upon securement of hook plate 40 across the fracture site.

Referring to FIG. 2C, prong region 56 of second hook member 45 has a longitudinal axis 55. Angled region 47 of elongated body 41 has a longitudinal axis 63. As shown in FIG. 2C, longitudinal axis 55 of second hook member 45 is substantially parallel to longitudinal axis 63 of angled region 47. Moreover, prong region 61 of first prong member 44 likewise has a longitudinal axis that is substantially parallel to longitudinal axis 63 of angled region 47. As explained in detail below, this parallel relationship is critical to allow hook plate 40 to seat congruently against the curved profile of the lateral malleolus as the hook members are impacted into a terminal fragment.

Figure 3A:
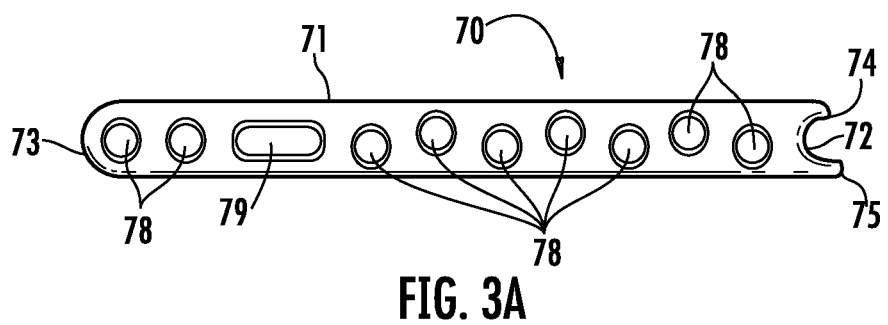
FIG. 3A is a top plan view of a 10-hole right offset fracture fixation plate of the present invention, configured for use in the fixation of certain fractures of the ankle.
Figure 3B:
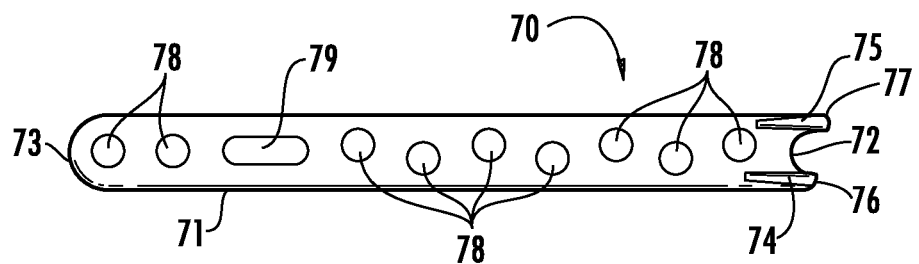
FIG. 3B is a bottom view of the 10-hole right offset fixation plate.

While, the example embodiment of the present invention shown in FIGS. 2A through 2F is configured for use in conjunction with fractures of the left fibula at the lateral malleolus, other configurations are also contemplated by the present invention. For example, FIGS. 3A and 3B show another, ten-hole embodiment of the present invention, configured for use in conjunction with fractures of the right lateral malleolus. Referring to FIGS. 3A and 3B, bone plate 70 is shown as comprising elongated body 71, having a first end 72 proximate first hook member, or tooth member 74 and second hook member, or tooth member 75, and a second end 75. Elongated body 71 includes a plurality of apertures therethrough for use in conjunction with conventional bone screws, including nine circular holes 78, and one slotted hole 79. First hook member 74 includes a first curved region having an apex 76. Second hook member 75 includes a curved region having an apex 77.

While bone plate 70 likewise displays bilateral asymmetry relative to its longitudinal axis, it is second hook member 75 having apex 77, on the right side of the bone plate, that is more distally spaced from first end 72 and second end 73 of elongated body 71. By way of contrast, in the previously described embodiment, it is first hook member 44 having apex 54, on the left side of the bone plate, that is more distally spaced from first end 42 and second end 43 of elongated body 41. This "mirror image" general configuration of bone plate 70, relative to bone plate 40, permits bone plate 70 to more closely approximate the curvilinear contoured distal surface of the right fibula at the lateral malleolus, upon securement of hook plate 70 across a fracture site.

Although both a six-hole left bone plate and a ten-hole right bone plate have been described above, other configurations of the present invention are also contemplated, including both left and right variations of bone plates, ranging in size from a four-hole bone plate, having an overall length of approximately 2.264 inches, to a twelve-hole bone plate, having an overall length of approximately 5.335 inches, or longer plates with more holes. Moreover, although, in preferred embodiments, each bone plate includes one slotted or oval hole for use in cooperation with bone screws, with the remaining holes being circular, other combinations of slotted and round bone screw accepting holes may alternatively be used. Alternatively, the hooks may be of identical length.

In a preferred embodiment, the hook plate of the present invention is constructed of wrought 18chromium-14nickel-2.5 molybdenum stainless steel, having a tensile strength of at least 135 Kips per square inch (KSI), and meeting the chemical and mechanical properties established by the ASTM-F139 standard. Other materials such as titanium, titanium alloy, or medical grade polymers may alternatively be used.

Figure 4:
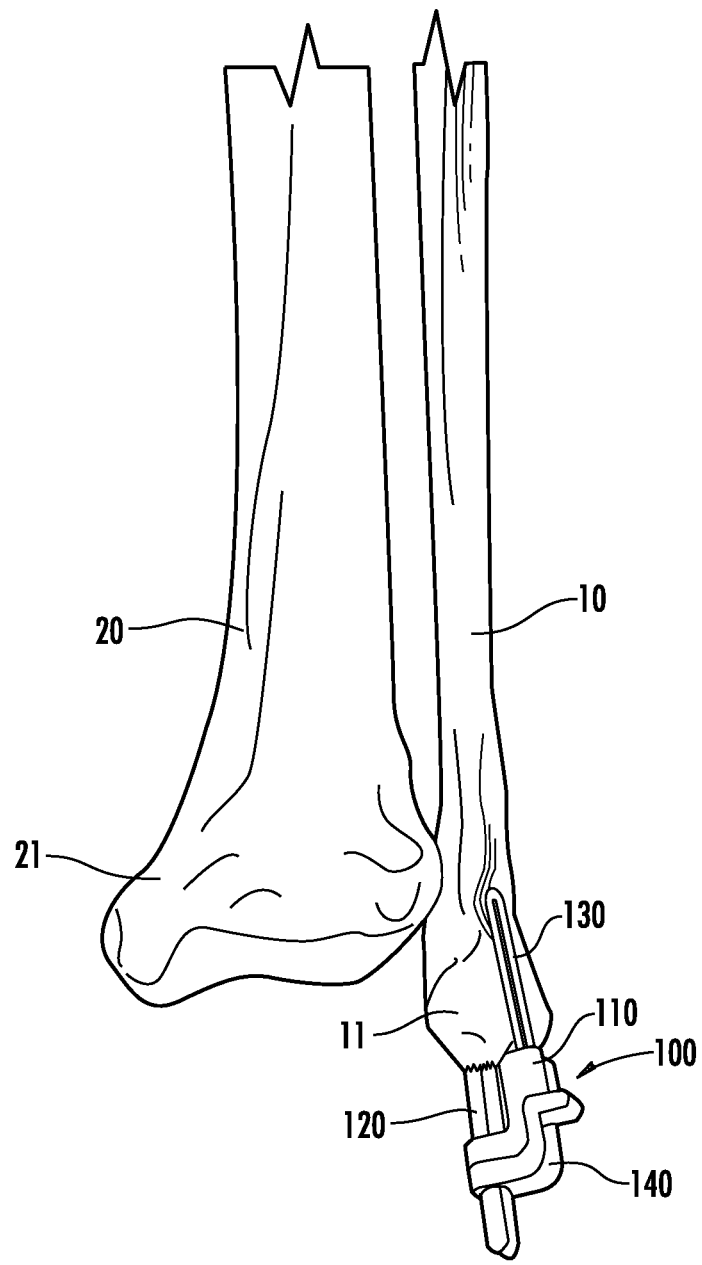
FIG. 4 is a perspective view of the double barreled drill guide of the present invention, shown positioned adjacent the lateral malleolus.
Figure 5:
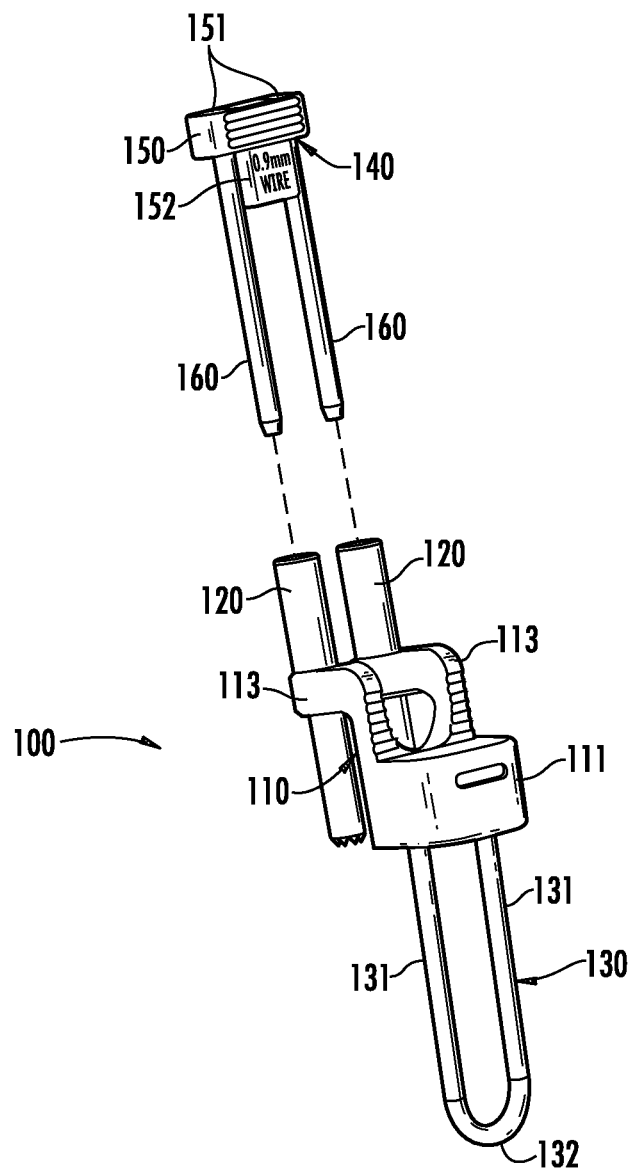
FIG. 5 is an exploded perspective view of the drill guide base assembly and interchangeable drill guide insert.

The present invention also comprises a double barreled drill guide, configured to direct a drill or K-wire in the proper depth and angle, relative to the lateral malleolus, such that, after pilot holes are drilled for the hook members and upon subsequently impacting the hook members of the present hook plate, the bottom surface of the hook plate tracks, and, when fully seated, is substantially adjacent, the surface contour of the lateral malleolus and the adjacent lateral surface of the fibula. The double barreled drill guide of the present invention is shown in FIGS. 4 and 5 as comprising drill guide base assembly 100. In addition, this guide may also be used with an interchangeable drill guide insert 140.

Figure 6:
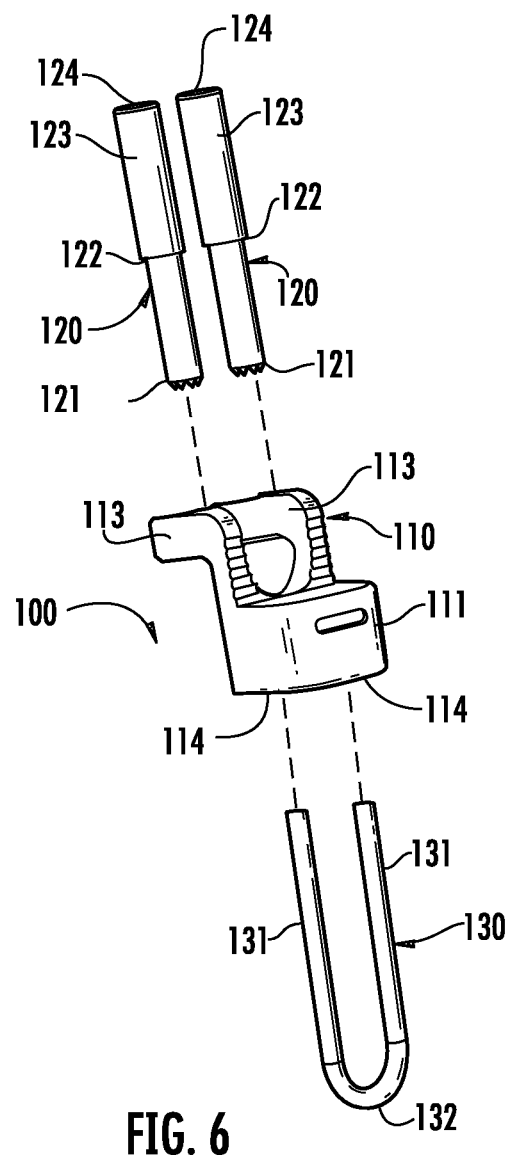
FIG. 6 is an exploded perspective view of the drill guide base assembly.
Figure 7A:
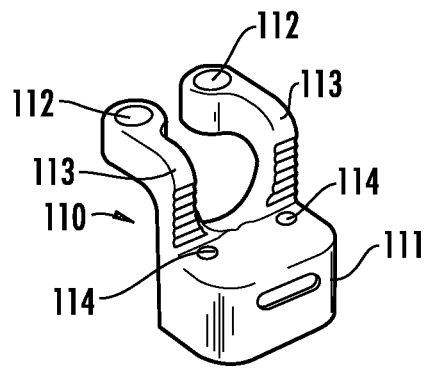
FIG. 7A is a perspective view of the body portion of the drill guide base assembly.
Figure 7B:
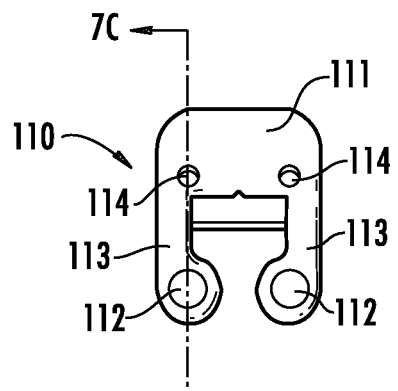
FIG. 7B is a back view of the body portion of the drill guide base assembly.
Figure 7C:
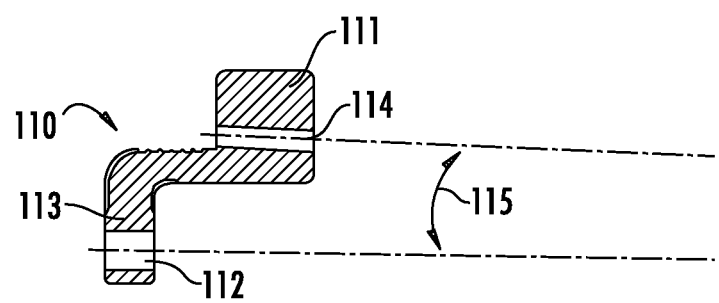
FIG. 7C is a sectional view of the body portion of the drill guide base assembly, taken generally along lines 7C-7C of FIG. 7B.

Drill guide base assembly 100 is shown in FIGS. 5 through 7C as comprising body portion 111, two base sleeves 120, and base positioning member 130. Body portion 111 has two apertures 114 extending therethrough, and two arm members 113, each having an associated aperture 112 extending therethrough. As shown in FIG. 7C, apertures 112 and 114 are canted slightly towards each other by a predetermined angle 115, relative to their respective longitudinal axes. In a preferred embodiment, predetermined angle 115 is a slight, acute approximately 3 degrees. This slight angle accounts for a certain amount of relative flex in the components of the drill guide and results in a substantially parallel alignment of the sleeves and the base positioning member upon application of the base positioning member against a superficial surface of the terminal end of the bone. In an alternative embodiment of the present invention, no predetermined angle 115 is employed, as the sleeves and base positioning member have longitudinal axes that are substantially parallel to each other. Upon assembly of drill guide base assembly 100, this, in turn, places each of base sleeves 120 at predetermined angle 115, canted towards base positioning member 130. This likewise places the sleeves of interchangeable drill guide insert 140 at predetermined angle 115, canted towards base positioning member 130, upon insertion of the drill guide insert 140 into base assembly 100. As a result, the two pilot holes for the hook members of the present invention are drilled at predetermined angle 115, relative to base positioning member 130. Body portion 113 is preferably constructed of a surgical stainless steel material, such as type 303 surgical stainless steel.

Base sleeve 120 is shown in FIG. 6 as comprising a generally tubular body having a first end 121, shoulder 122, collar region 123, and second end. First end 121 has a chamfered and serrated configuration, permitting drill guide base assembly 100 to grip the distal surface of the lateral malleolus when positioned prior to drilling pilot holes for the hook members of the bone plate as shown in FIG. 4, serving to inhibit unwanted slippage of the overall drill guide. An internal channel communicates between openings at first end 121 and second end 122, and is sized to axially receive a drill. In a preferred embodiment, collar region 123 has a length of approximately 0.400 inches, and base sleeve 120 has an overall length of approximately 1.025 inches. Base sleeve 120 is preferably constructed of a surgical stainless steel material, such as type 455 surgical stainless steel, condition H-900.

As shown in FIG. 6, base positioning member 130 is substantially U-shaped, having two elongated arms 131 and U-shaped end 132. Base positioning member 130 is preferably constructed of a stainless steel material, such as type 316LS stainless steel having a minimum ultimate tensile strength of 160 KSI. In another embodiment, base positioning member 130 may be of the form of a plate having a contoured surface approximating the contoured elongated body of the bone plate to be implanted, or one or more pins (not shown).

Drill guide base assembly 100 is assembled by press fitting each base sleeve 120 though an associated aperture 112 of arm 113 of body portion 111, until shoulder 122 rests adjacent a top surface of arm 113. Base positioning member 130 is affixed to body portion 111 by inserting each elongated arm 131 through an associated aperture 114 of body portion 111, and then welding base positioning member in place using a nickel or other suitable braze.

Figure 8A:
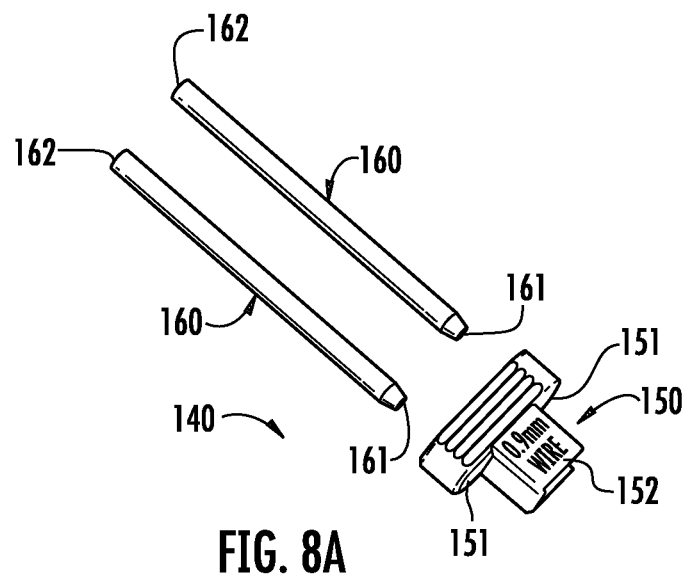
FIG. 8A is an exploded perspective view of the interchangeable guide wire insert.
Figure 8B:
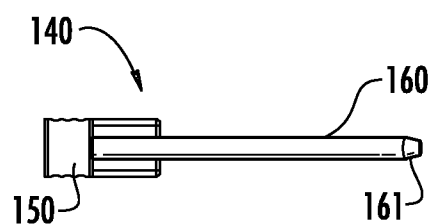
FIG. 8B is a side view of the interchangeable guide wire insert.

Interchangeable drill guide insert 140 is shown in FIGS. 8A and 8B as comprising generally T-shaped body 150 and two tubular insert sleeves 160. T-shaped body 150 includes two apertures 151 extending therethrough, each accepting an associated insert sleeve 160, which is assembled by press-fitting each inner sleeve 160 into an associated aperture 151. Two inwardly curving recesses extending along T-shaped body 150 have a radius of curvature coinciding with the exterior surface of collar region 123 of base sleeve 120 of drill guide base assembly 100, serving to further secure interchangeable drill guide insert 140 to drill guide base assembly 100, as tubular insert sleeves 160 are advanced within associated base sleeves 120 until T-shaped body 150 is fully seated adjacent body portion 111 of drill guide base assembly 100. T-shaped body 150 is preferably constructed of a surgical stainless steel material, such as type 303 surgical stainless steel.

Each insert sleeve 160 includes a tapered first end 161, second end 162, and an internal channel communicating between openings at first end 161 and second end 162. This internal channel is sized to accommodate a guide wire of a predetermined size, such as a 0.9 millimeter Kirshner wire, or K-wire, to be used in conjunction with a 2.0 mm cannulated drill that is subsequently guided over the wire upon removal of the double barreled drill guide, creating the pilot holes to accept axial impacting of the hook members of the present bone plate. This, in turn, gives the surgeon the option of either drilling holes directly into the terminal bone fragment using a non-cannulated drill by using guide assembly 100 without the insert 140, or, if less speed and greater potential precision is desired, to first insert a K-wire, and then pass a cannulated drill over the wire by using guide assembly 100 with insert 140. In a preferred embodiment of the present invention, insert sleeve 150 is approximately 1.150 inches in length. Insert sleeve 160 is preferably constructed of a surgical stainless steel material, such as type 455 surgical stainless steel, condition H-900.

As shown in FIG. 8A, T-shaped body 150 includes laser-etched indicia 152, indicating the size of guide wire accommodated by the present interchangeable drill guide insert 140, in this case a 0.9 millimeter guide wire. Moreover, as other interchangeable drill and guide wire inserts of varying sizes may alternatively be used, laser-etched indicia 152 is changed as necessary indicate the particular drill or guide wire size for each variation of interchangeable drill guide insert 140.

In addition to releasably accepting interchangeable drill guide insert 140, drill guide base assembly 100 also releasably accepts a reversible gauge assembly 170, shown in FIGS. 9A through 9C as comprising T-shaped gauge body 180, first cylindrical elongated member, or trocar 190 having tapered end 191, and second cylindrical elongated member, or trocar 200 having tapered end 201. T-shaped body 180 includes two apertures 181 extending therethrough, each accepting an associated cylindrical trocar, and is assembled by press-fitting the trocars into associated apertures. Two inwardly curving recesses extending along T-shaped body 180 have a radius of curvature coinciding with the exterior surface of collar region 123 of base sleeve 120 of drill guide base assembly 100, serving to further secure gauge assembly 170 to drill guide base member 100, as cylindrical trocars 190 and 200 are advanced within associated base sleeves 120 until T-shaped body 180 is fully seated adjacent body portion 111 of drill guide base member 100. T-shaped body 180 further includes laser etched indicia 183 and 184, indicating "LEFT" and "RIGHT", respectively, on opposing sides of the T-shaped body. T-shaped body 180 is preferably constructed of a surgical stainless steel material, such as type 303 surgical stainless steel.

As shown in FIGS. 9A through 9C, first trocar 190 and second 200 are of different lengths, with first trocar 190 being longer than trocar 200. In a preferred embodiment, first trocar 190 is approximately 2 mm longer than second trocar 200, with first trocar being approximately 1.273 inches in length, and second trocar being approximately 1.150 inches in length. This differential permits a surgeon, prior to drilling any pilot holes, to use reversible gauge assembly 170 to confirm appropriate use of either a left or right offset hook plate of the present invention to properly accommodate the inclination of the bone curvature at the entry sites for the hooks and permit the hook plate to be properly seated adjacent the fibula upon impacting the hook members. In particular, once the double barreled drill guide is positioned adjacent the lateral malleolus as shown in FIG. 4, gauge assembly 170 is inserted into drill guide base assembly 100. Upon insertion, if the indicia 183 or 184 facing laterally, or outwardly is a correct indication of the left versus right offset hook plate to be used, the differential in lengths of trocars 190 and 200 will approximate the curvature of the lateral malleolus at the distal end of the fibula, and gauge assembly 170 will be substantially fully seated within base assembly 100. If, however, gauge assembly 170 does not substantially fully seat within base assembly 100, this is a visual indication that, since the differential in length of the trocars does not follow the contoured distal surface of the lateral malleolus, the indicia facing outwardly or laterally is most likely incorrect. In this case, the gauge assembly 170 can be withdrawn and flipped, and then reinserted to determine if the opposite offset hook plate is required. If the gauge assembly fully seats, it is indicative of the proper offset plate to use. If the gauge assembly does not seat when inserted with either attitude, it is indicative that a zero offset, bilaterally symmetrical plate is required.

Figure 10:
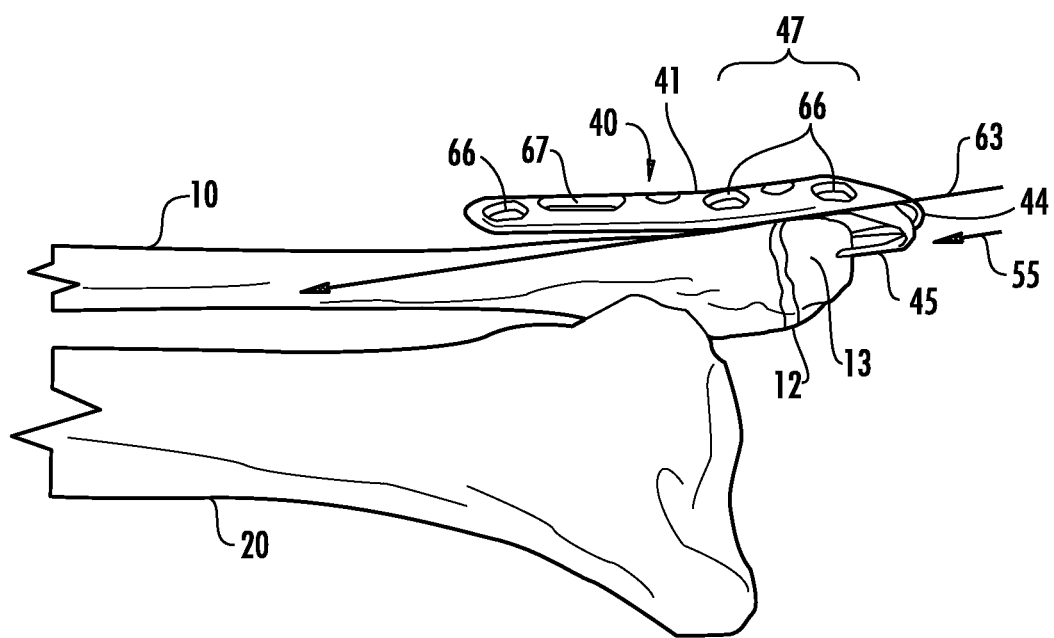
FIG. 10 is an anterior view, looking posteriorly, of the left tibia and fibula and showing, in particular, a 6-hole fracture fixation plate positioned immediately prior to impacting the hook members and affixation of the plate to the left fibula.
Figure 11:
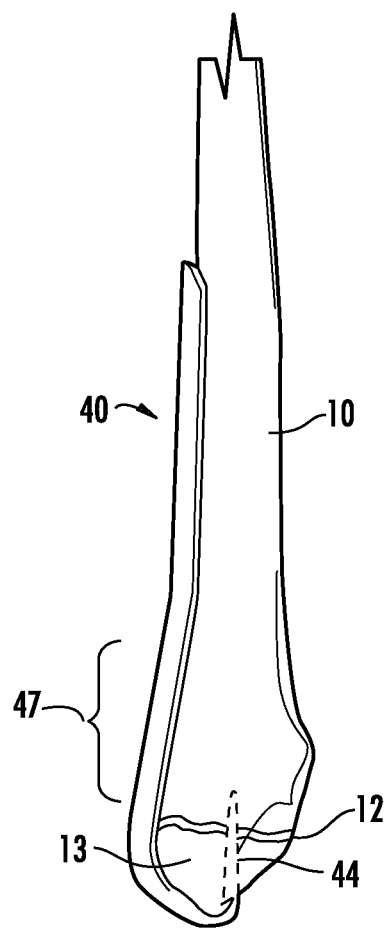
FIG. 11 is an anterior view of the right fibula showing, in particular, the positioning of the 6-hole fracture fixation plate following implantation and reduction of the fracture of the lateral malleolus in which the prong regions cross the fracture site.
Figure 12:
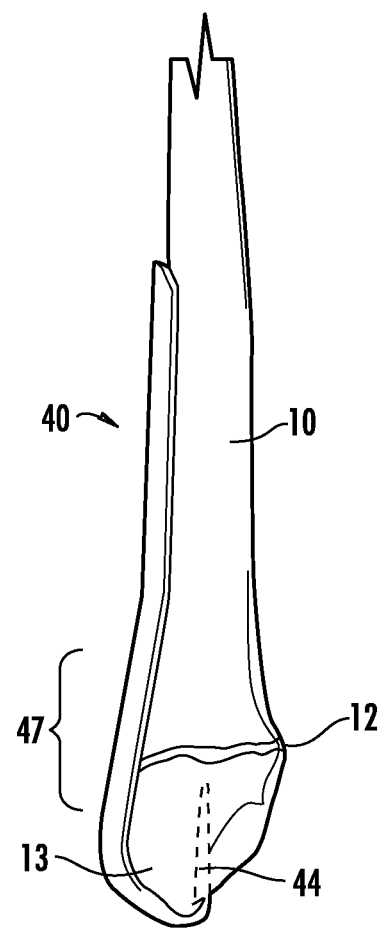
FIG. 12 is an anterior view of the right fibula showing, in particular, the positioning of the 6-hole fracture fixation plate following implantation and reduction of the fracture of the lateral malleolus in which the prong regions do not cross the fracture site.

As shown in FIG. 10, once the pilot holes are drilled using the double barreled drill guide (or once K-wires are positioned using the drill guide, and a cannulated drill is advanced over the wire to prepare the pilot holes), hook members 44 and 45 of hook plate 40 are longitudinally advanced into the pilot holes along longitudinal axis 55 of the hook members, using a hammer or other suitable instrument. Since the drill guide references the proper entry site and trajectory of the drill holes, impaction of the plate 40 into bone causes the plate to advance along longitudinal axis 63. When fully seated, first region 46, second region 48, and intermediate angled region 47 come to lie congruently along the curved surface of the bone. This anatomic fit of the plate against the bone is the result of designing the longitudinal axis 55 of the hooks to be parallel to the longitudinal axis 63 of the intermediate region 47, and to the creation of the specific entry site in the bone using the double barreled guide assembly 70 that matches the depth and trajectory of hooks 44 and 45. Following full axial insertion of the hook members, this, in turn, causes elongated body 41 of hook plate 40 to come to rest substantially adjacent the distal end of the fibula, with longitudinal axis 63 of angled region 47 substantially parallel to and coinciding with the flared end of the fibula at the lateral malleolus, as shown in FIGS. 11 and 12. Bone screws are then placed through appropriate circular and slotted holes of hook plate 40 and into the fibula, as desired, to secure hook plate 40 in place.

Although, as described above, a drill is used to prepare pilot holes in the lateral malleolus to receive the hook members, for patients with relatively soft bone, a surgeon may potentially opt to forego the preparation of pilot holes, and axially hammer the hook members of the bone plate of the present invention directly into place. Moreover, although the embodiment of the present invention discussed above is designed for use in conjunction with fractures of the lateral malleolus of the fibula, it may also be used in the configuration discussed above in conjunction with fractures of the medial malleolus of the tibia or other sites as discussed previously. Moreover, the overall lengths of the angled region, first region and second region of the elongated body, as well as the relative angles of the angled region with respect to the adjacent first and second regions of the elongated body, may be modified to more closely accommodate the terminal ends of other bones, such as the medial malleolus of the tibia, for the treatment of fractures thereof.

The present invention also comprises kits of combinations of the components described above. For example, a plurality of hook plates of multiple sizes, from four-hole to fifteen-hole embodiments in both left and right offset variations, and possibly with zero offset variations, may be provided in kit form so that appropriately sized and configured hook plates of the present invention are readily available at a hospital or trauma center. Moreover, one or more hook plates may be provided in kit form in combination with the double barreled drill guide of the present invention. Furthermore, the double barreled drill guide, either alone or as a part of a kit of one or more hook plates, may itself be provided as a kit or sub-kit including the base assembly, interchangeable drill guides sized to accommodate guide wires and/or non-cannulated drills of varying sizes, and the gauge assembly.

Although the present invention has discussed plates with two hooks, it will be understood by those skilled in the art that other embodiments having one hook or a plurality of hooks are possible and do not depart from the scope or spirit of the present invention.

The preceding description and drawings merely explain the invention and the invention is not limited thereto, as those of ordinary skill in the art who have the present disclosure before them will be able to make changes and variations thereto without departing from the scope of the present invention.

What is claimed is:

1. A bone plate for fixing fractures having a small terminal fragment, comprising:
   an elongated body having a first end, a second end, a top surface, and a bottom surface; and
   at least two hook members proximate the first end, each of the hook members having an associated apex;
   wherein the distance between the second end and the apex of one of the hook members is greater than the distance between the second end and the apex of another of the hook members.

2. The invention according to claim 1, wherein the elongated body has a flared region disposed between the first end and the second end, the flared region having a first longitudinal axis;
   at least one of the hook members has a prong region having a second longitudinal axis; and
   wherein the first longitudinal axis and the second longitudinal axis are substantially parallel to each other.

3. The invention according to claim 2, wherein the elongated body includes a first region and a second region on opposing sides of the flared region, and wherein the first region, flared region, and second region collectively substantially correspond to a surface contour of a human bone proximate its terminal end.

4. The invention according to claim 3, wherein the human bone is a lateral malleolus.

5. The invention according to claim 3, wherein the human bone is a medial malleolus.

6. The invention according to claim 3, wherein the human bone is a proximal ulna.

7. The invention according to claim 1, wherein the elongated body includes at least one bone screw accepting hole extending therethrough.

8. The invention according to claim 1, wherein at least a portion of a bottom surface of the elongated body has a concave curvature in a direction transverse to a predominantly longitudinal axis of the elongated body.

9. The invention according to claim 1, wherein at least one hook member comprises a curved region curving from the elongated body proximate the first end, back towards the second end of the elongated body and terminating in a prong region.

10. The invention according to claim 1, wherein the elongated body has a profile substantially conforming to a three-dimensional scan of a portion of a human bone.

11. The invention according to claim 1, wherein the elongated body has a profile substantially corresponding to a three-dimensional scan of a model of a portion of a human bone.

12. The invention according to claim 1, wherein the elongated body has a profile substantially confirming to a mathematical model of a portion of a human bone.

\* \* \* \* \*